United States Patent
Frech et al.

(10) Patent No.: US 10,678,613 B2
(45) Date of Patent: Jun. 9, 2020

(54) SYSTEM AND METHOD FOR DYNAMIC CONTROL OF WORKFLOW EXECUTION

(71) Applicant: Seven Bridges Genomics, Inc., Cambridge, MA (US)

(72) Inventors: Christian Frech, Brookline, MA (US); Raunaq Malhotra, Brighton, MA (US)

(73) Assignee: SEVEN BRIDGES GENOMICS INC., Charlestown, MA (US)

(*) Notice: Subject to any disclaimer, the term of this patent is extended or adjusted under 35 U.S.C. 154(b) by 0 days.

(21) Appl. No.: 16/176,833

(22) Filed: Oct. 31, 2018

(65) Prior Publication Data
US 2019/0129769 A1    May 2, 2019

Related U.S. Application Data

(60) Provisional application No. 62/579,181, filed on Oct. 31, 2017.

(51) Int. Cl.
*G06F 9/54*     (2006.01)
*G06F 9/451*    (2018.01)
(Continued)

(52) U.S. Cl.
CPC ............... *G06F 9/543* (2013.01); *G06F 8/34* (2013.01); *G06F 8/36* (2013.01); *G06F 9/451* (2018.02);
(Continued)

(58) Field of Classification Search
CPC ..................................................... G06F 9/541
(Continued)

(56) References Cited

U.S. PATENT DOCUMENTS 7,100,147 B2    8/2006  Miller et al.
7,451,432 B2    11/2008 Shukla et al.
(Continued)

FOREIGN PATENT DOCUMENTS

KR    101282798 B1    7/2013
WO    2010010992 A1   1/2010
(Continued)

OTHER PUBLICATIONS

Abouelhoda, 2012, Tavaxy: integrating Taverna and Galaxy workflows with cloud computing support, BMC Bioinformatics 13:77.
(Continued)

*Primary Examiner* — Andy Ho
(74) *Attorney, Agent, or Firm* — Morgan, Lewis & Bockius LLP

(57) ABSTRACT

Some embodiments relate to systems for processing one or more computational workflows. In one embodiment, a description of a computational comprises a plurality of applications, in which applications are represented as nodes and edges connect the nodes indicate the flow of data elements between applications. A task execution module is configured to create and execute tasks. An application programming interface (API) is in communication with the task execution module and comprises a plurality of function calls for controlling at least one function of the task execution module. An API script includes instructions to the API to create and execute a plurality of tasks corresponding to the execution of the computational workflow for a plurality of samples. A graphical user interface (GUI) is in communication with the task execution module and configured to receive input from an end user to initiate execution of the API script.

20 Claims, 10 Drawing Sheets

(51) Int. Cl.
  *G06F 16/901*    (2019.01)
  *G06F 8/36*     (2018.01)
  *G06F 8/34*     (2018.01)
  *G16B 50/00*    (2019.01)

(52) U.S. Cl.
  CPC .......... *G06F 16/9024* (2019.01); *G16B 50/00* (2019.02)

(58) Field of Classification Search
  USPC ........................................................ 719/328
  See application file for complete search history.

(56) References Cited

U.S. PATENT DOCUMENTS

| | | | |
|---|---|---|---|
| 7,577,554 | B2 | 8/2009 | Lystad et al. |
| 7,620,800 | B2 | 11/2009 | Huppenthal et al. |
| 7,885,840 | B2 | 2/2011 | Sadiq et al. |
| 8,146,099 | B2 | 3/2012 | Tkatch et al. |
| 8,639,847 | B2 | 1/2014 | Blaszczak et al. |
| 9,184,988 | B2 | 11/2015 | Bartlett et al. |
| 9,250,886 | B2 | 2/2016 | Gnech et al. |
| 9,436,922 | B2 | 9/2016 | Agarwal et al. |
| 9,519,884 | B2 | 12/2016 | Aron et al. |
| 9,558,321 | B2 | 1/2017 | Tijanic et al. |
| 2002/0133504 | A1 | 9/2002 | Vlahos et al. |
| 2004/0078105 | A1 | 4/2004 | Moon et al. |
| 2004/0243982 | A1 | 12/2004 | Robison |
| 2005/0282137 | A1 | 12/2005 | Sasinowski et al. |
| 2013/0232480 | A1 | 9/2013 | Winterfeldt et al. |
| 2013/0332081 | A1 | 12/2013 | Reese et al. |
| 2014/0200147 | A1 | 7/2014 | Bartha et al. |
| 2014/0281708 | A1* | 9/2014 | Adam ................. G06F 11/1443 714/18 |
| 2015/0020061 | A1 | 1/2015 | Ravi |
| 2015/0066381 | A1 | 3/2015 | Kural |
| 2015/0066383 | A1 | 3/2015 | Wernicke |
| 2015/0161536 | A1 | 6/2015 | Mikheev |
| 2016/0011905 | A1 | 1/2016 | Mishra et al. |
| 2016/0092632 | A1* | 3/2016 | Zhou ..................... G06F 19/321 705/3 |
| 2016/0103659 | A1 | 4/2016 | Tijanic et al. |
| 2016/0313874 | A1 | 10/2016 | Mikheev |
| 2017/0199764 | A1 | 7/2017 | Tijanic et al. |

FOREIGN PATENT DOCUMENTS

| | | |
|---|---|---|
| WO | 2013035904 A1 | 3/2013 |
| WO | 2016060910 A1 | 4/2016 |
| WO | 2016182578 A1 | 11/2016 |

OTHER PUBLICATIONS

Agarwal, 2013, SINNET: Social Interaction Network Extractor from Text, Proc IJCNLP 33-36.
Balhajjame et al., Using a suite of ontologies for preserving workflow-centric research objects, Web Semantics: Science, Services, and Agents on the World Wide Web, 2015, 16-42.
Cock, 2013, Galaxy tools and workflows for sequence analysis with applications in molecular plant pathology, Peer J 1: e167.
Cohen-Boulakia, 2014, Distilling structure in Taverna scientific workflows: a refactoring approach, BMC Bioinformatics 15(Suppl 1):S12.
Cromwell: A Workflow Management System geared towards scientific workflows. Available at: https://github.com/broadinstitute/cromwell/blob/29_hotfix/README.md. Accessed Sep. 26, 2017.
Deelman et al., Pegasus, a workflow management system for science automation, Future Generation Computer Systems, 2015, 17-35.
Delcher, 1999, Alignment of whole genomes, Nucl. Acids Res 27(11):2369-76.
Dinov, 2011, Applications of the pipeline environment for visual informatics and genomic computations, BMC Bioinformatics 12:304
Dinov, 2014, The perfect neuroimaging-genetics-computation storm: collision of petabytes of data, millions of hardware devices and thousands of software tools, Brain Imaging and Behavior 8:311-322
Dudley, 2009, A quick guide for developing effective bioinformatics programming skills, PLoS Comput Biol 5(12): e1000589.
Durham, 2005, EGene: a configurable pipeline system for automated sequence analysis, Bioinformatics 21(12):2812-2813.
Fiers, 2008, High-throughput Bioinformatics with the Cyrille2 Pipeline System, BMC Bioinformatics 9:96.
Goecks et al., Galaxy: a comprehensive approach for supporting accessible, reproducible, and transparent computational research in the life sciences, Genome Biology, 2010.
Guo, A workflow task scheduling algorithm based on the resources' fuzzy clustering in cloud computing environment, International Journal of Communication Systems (Abstract only), 2015, 28:1053-1067.
Hettne et al., Structuring research methods and data with the research object model: genomics workflows as a case study, Journal of Biomedical Semantics, 2014, 5:41.
Hokamp, 2003, Wrapping up BLAST and Other Applications for Use on Unix Clusters, Bioinformatics 19(3)441-42.
Hoon, 2003, Biopipe: A flexible framework for protocol-based bioinformatics analysis, Genome Res 13(8):1904-1915.
Hull, 2006, Taverna: a tool for building and running workflows of services, Nucl Acids Res 34(Web Server issue): W729-32.
International Search Report and Written Opinion dated Jan. 5, 2016, for International Patent Application PCT/US2015/054461 with International Filing Date Oct. 7, 2015, (7 pages)
Kano, 2010, Text mining meets workflow: linking U-Compare with Taverna, Bioinformatics 26(19):2486-7.
Kanwal et al., Challenges of large-scale biomedical workflows on the cloud—a case study on the need for reproducibility of results, Computer-Based Medical Systems (CBMS), 2015 IEEE 28th International Symposium, 2015.
Kaushik et al., Rabix: an open-source workflow executor supporting recomputability and interoperability of workflow descriptions, Pac Symp Biocomput, 2016, 22:154-165.
Kawas, 2006, BioMoby extensions to the Taverna workflow management and enactment software, BMC Bioinformatics 7:523.
Koster et al., Snakemake—a scalable bioinformatics workflow engine, Bioinformatics, 2012, vol. 28, No. 19, pp. 2520-1522.
Krabbenhoft, 2008, Integrating ARC grid middleware with Taverna workflows, Bioinformatics 24(9):1221-2.
Kuhn, 2010, CDK-Taverna: an open workflow environment for cheminformatics, BMC Bioinformatics 11:159.
Kurs et al., Nextflow Workbench: Reproducible and Reusable Workflows for Beginners and Experts, bioRxiv, 2016.
Lanzen, 2008, The Taverna Interaction Service: enabling manual interaction in workflows, Bioinformatics 24 (8):1118-20.
Leipzig, A review of bioinformatic pipeline frameworks, Briefings in Bioinformatics, 2017, 18(3), 530-536.
Li, 2008, Automated manipulation of systems biology models using libSBML within Taverna workflows, Bioinformatics 24(2):287-9.
Li, 2008, Performing statistical analyses on quantitative data in Taverna workflows: an example using R and maxdBrowse to identify differentially-expressed genes from microarray data, BMC Bioinformatics 9:334.
Li, 2010, A survey of sequence alignment algorithms for next-generation sequencing, Briefings in Bionformatics 11 (5):473-483.
Machine translation of KR 10-1282798 B1 generated on Jan. 6, 2016, by the website of the European Patent Office (23 pages).
Machine translation produced on Jun. 1, 2015, by Espacenet of WO 2010/010992 A1 (11 pages).
Machine translation produced on Jun. 1, 2015, by WPIO website of WO 2013/035904 (10 pages).
McKenna, 2010, The Genome Analysis Toolkit: a MapReduce framework for analyzing next-generation DNA sequencing data, Genome Res 20(9):1297-1303.
Missier, 2010, Taverna, reloaded, Proc. Scientific and Statistical Database Management, 22nd Int Conf, Heidelberg, Germany, Jun./Jul. 2010, Gertz & Ludascher, Eds., Springer.

(56) References Cited

OTHER PUBLICATIONS

Nenadic, 2010, Nested Workflows, The Taverna Knowledge Blog, Dec. 13, 2010. Retrieved on Feb. 25, 2016 from http://taverna.knowledgeblog.org/2010/12/13/nested-workflows/.
O'Driscoll et al. 'Big Data,' Hadoop and cloud computing in genomics, 2013, pp. 774-781, vol. 46, Journal of Informatics Biomedical.
Oinn, 2004, Taverna: a tool for the composition and enactment of bioinformatics workflows, Bioinformatics 20(17):3045-54.
Oinn, 2006, Taverna: lessons in creating a workflow environment for the life sciences, Concurrency and Computation: Practice and Experience 18(10):1067-1100.
O'Rawe, 2013, Low Concordance of Multiple Variant-Calling Pipelines: Practical Implications for Exome and Genome Sequencing, Genome Med 5:28.
Pabinger, 2013, A survey of tools for variant analysis of next-generation genome sequencing data, Brief Bioinf.
Paterson, 2009, An XML transfer schema for exchange of genomic and genetic mapping data: implementation as a web service in a Taverna workflow, BMC Bioinformatics 10:252.
Peng, Reproducible Research in Computational Science, Science, Dec. 2, 2011, 334(6060), 1226-1227.
Potter, 2004, The ensemble analysis pipeline, Genome Res 14:934-941.
Ramirez-Gonzalez, 2011, Gee Fu: a sequence version and web-services database tool for genomic assembly, genome feature and NGS data, Bioinformatics 27(19):2754-2755.
Rex, 2003, The LONI Pipeline Processing Environment, Neuroimage 19: 1033-1048.
Sandve et al., Ten Simple Rules for Reproducible Computational Research, PLoS Computational Biology, Oct. 2013, vol. 9, Issue 10, e1003285.
Schenk, 2013, A pipeline for comprehensive and automated processing of electron diffraction data in IPLT, J Struct Biol 182(2):173-185.
Sroka, 2006, XQTav: an XQuery processor for Taverna environment, Bioinformatics 22(10):1280-1.
Sroka, 2010, A formal semantics for the Taverna 2 workflow model, J Comp Sys Sci 76(6):490-508.
Sroka, 2011, CalcTav—integration of a spreadsheet and Taverna workbench, Bioinformatics 27(18):2618-9.
Stallman, GNU Make: A Program for Directing Recompilation, Free Software Foundation, Inc., Jul. 2002.
Tan, 2010, A Comparison of Using Taverna and BPEL in Building Scientific Workflows: the case of caGrid, Concurr Comput 22(9):1098-1117.
Tan, 2010, CaGrid Workflow Toolkit: a Taverna based workflow tool for cancer grid, BMC Bioinformatics 11:542.
Terstyanszky et al., Enabling scientific workflow sharing through coarse-grained interoperability, Future Generation Computer Systems, 2014, 37, 46-59
The Free Dictionary.com, Article about Client-server system originally from IGEL Technologies (2009) entitled: White Paper Cloud Computing: Thin clients in the cloud, Oct. 20, 2016 retrieval date; pp. 1-2.
The Free Dictionary.com, Article about Cloud computing originally from the Columbia Electronic Encyclopedia (2013) Oct. 20, 2016 retrieval date; Columbia Univ. Press—pp. 1-3.
Torri, 2012, Next generation sequence analysis and computational genomics using graphical pipeline workflows, Genes (Basel) 3(3):545-575.
Truszkowski, 2011, New developments on the cheminformatics open workflow environment CDK-Taverna, J Cheminform 3:54.
Turi, 2007, Taverna Workflows: Syntax and Semantics, IEEE Int Conf on e-Science and Grid Computing 441-448.
Vivian et al., Rapid and efficient analysis of 20,000 RNA-seq samples with Toil, bioRxiv, 2016.
Warneke et al., Nephele: Efficient Parallel Data Processing in the Cloud, ACM, 2009.
Wassink, 2009, Using R in Taverna: RShell v1.2. BMC Res Notes 2:138.
Wen, 2012, Comparison of Open-Source Cloud Management Platforms: OpenStack and OpenNebula, 9th International Conference on Fuzzy Systems and Knowledge Discovery.
Wolstencroft, 2005, Panoply of Utilities in Taverna, Proc 2005 1st Int Conf e-Science and Grid Computing 156-162.
Wolstencroft, 2013, The Taverna Workflow Suite: Designing and Executing Workflows of Web Services on the Desktop Web or in the Cloud, Nucl Acids Res 41(W1):W556-W561.
Yildiz, 2014, BIFI: a Taverna plugin for a simplified and user-friendly workflow platform, BMC Res Notes 7:740.
Yu, 2007, A tool for creating and parallelizing bioinformatics pipelines, DOD High Performance Computing Conf 417-420.
Zhang, 2013, Taverna Mobile: Taverna workflows on Android, EMBnet J 19(B):43-45.
Zhao, 2012, Why Workflows Break-Understanding and Combating Decay in Taverna Workflows, eScience 2012, Chicago, Oct. 2012.

\* cited by examiner

SYSTEM AND METHOD FOR DYNAMIC CONTROL OF WORKFLOW EXECUTION

RELATED APPLICATIONS

This application claims priority to U.S. Provisional Patent Application Ser. No. 62/579,181 filed on Oct. 31, 2017, the contents of which are hereby incorporated by reference in their entirety.

FIELD

Aspects of the technology described herein relate to workflow processing systems, such as workflow processing systems for executing computational workflows.

BACKGROUND

Various workflow execution services exist for conducting bioinformatics analyses. Often, the workflow execution service is in a cloud-based environment, and provides a central hub for teams to store, analyze, and jointly interpret their bioinformatic data. The service may co-locate analysis pipelines alongside the largest genomic datasets to optimize processing. It may allocate storage and compute resources on demand, to meet the needs of ever-growing analyses. Further, the service may include a Graphical User Interface (GUI) that allows a user to create projects, run tasks, upload and manage project members, and so on. Additionally, the service may include an Application Programming Interface (API) that allows for these procedures to be carried out programmatically with additional logic, and a Command Line Interface (CLI) that allows for interactive control. Typically, end users may use only a single interface for performing the bulk of their analyses.

An API allows for end users to design and configure complex, multi-stage, or large batch analyses without using the GUI. In most workflow execution services, any action that can be taken using the GUI can be executed using the API, but the API allows for additional user-generated logic. Typically, a user interacts with the API using an API client (e.g., Postman), a programming language (e.g., Python), or via the terminal of their computer by using a command line program (e.g., cURL). API commands can be chained together to form an API script, allowing for the automation and integration of various service features. For example, an API script can include steps directed towards data upload, project management, metadata capture, quality control (QC) checks, execution of tools and workflows, and handling of the resulting data. In this way, the API offers many advantages over the GUI via programmatic access and automation, allowing for the creation of complex processes and workflows that would be not be practicable or cost efficient to implement as a GUI feature.

Though the API has many advantages over other modes of interaction, it lacks several benefits conferred using the GUI. For example, The API may not be accessible to those lacking programming expertise. Further, API scripts are typically executed by external client computers which interact with the service over a network. The client computer typically lacks the persistence and stability of the service, which may be subject to extensive quality testing and validation and include multiple levels of redundancy. The client machine often has no logs (and thus is hard to troubleshoot), may inadvertently reboot, and is subject to user error or misuse. Additionally, as the API includes features not present in the GUI, those interacting with the service only with its GUI are unable to take advantage of the advanced features. Accordingly, there is a need for improvements in the interface to and control of workflow execution services.

SUMMARY

Accordingly, the inventors have recognized and appreciated that these problems may be solved by incorporating an API script directly into a workflow execution service, resulting in several advantages over singular interface workflow execution that improves the operation of both the API and other modes of interaction together. This results in the ability to build and execute computational workflows which provide for programmatic access and automation, while retaining the benefits of server-side execution, control, and ease of use. In effect, the API script causes the workflow execution service to instruct itself to perform complex analyses that may not be possible using other modes of interaction, such as via the GUI or CLI; however, the GUI or CLI may be used to initiate, control, or observe its operation, providing a simple way for end users to incorporate complex analyses into their work streams.

In one embodiment, a system for processing one or more computational workflows comprises a non-transitory storage medium connected to a processor. The storage medium stores a description of a computational workflow comprising a directed acyclic graph (DAG) in which applications are represented as nodes and edges connecting the nodes indicate the flow of data elements between linked applications. A task execution module is configured to create and execute tasks, wherein a single execution of the computational workflow comprises a single task. An application programming interface (API) is in communication with the task execution module and comprises a plurality of function calls for controlling at least one function of the task execution module. The storage medium further comprises an API script for automating functions of the task execution module, and includes instructions to the API to create and execute a plurality of tasks corresponding to the execution of the computational workflow for a plurality of samples. A GUI is in communication with the task execution module, wherein the GUI is configured to receive input from an end user to initiate execution of the API script.

In some embodiments, the API script further comprises instructions to collect the outputs of the computational workflow for each of the plurality of samples, and process the outputs using a second computational workflow. In another embodiment, the API script further comprises instructions to determine whether a sample of the plurality of samples has already been processed by the computational workflow. In one embodiment, the API script requires one or more input files for execution, and the GUI is further configured to receive the one or more input files from the end user. In this embodiment, the one or more input files from the end user comprises a sample sheet defining the location of a plurality of samples to be processed by the computational workflow. In another embodiment, the API script further comprises instructions to execute a different computational workflow for a sample depending on characteristics of the sample. In this embodiment, the characteristic of the sample considered by the API script is the file format for a sample. In some embodiments, each sample comprises a data file, each data file comprising a plurality of DNA sequence reads. In another embodiment, the API script further comprises an API client, wherein the API client comprises a plurality of wrappers for API calls. In further embodiments, the API script further comprises monitoring the plurality of tasks, identifying a task that has failed, and restarting the failed task. In another embodiment, the instructions in the API script further comprise retrieving a data file for task corresponding to a sample from an external resource.

In some embodiments, a method for executing one or more computational workflows comprises representing, in a storage medium connected to a processor, a computational workflow as a directed acyclic graph (DAG) in which applications are represented as nodes and edges connecting the nodes indicate the flow of data elements between linked applications. A request is received from an end user via a graphical user interface (GUI) to initiate execution of an Application Programming Interface (API) script. The API script comprises instructions to direct a task execution module connected to the processor to create and execute a plurality of tasks corresponding to the execution of the computational workflow for a plurality of samples. The processor executes the instructions within the API script, and subsequently receives from the API script a plurality of requests to create and execute a plurality of tasks corresponding to the execution of the computational workflow for the plurality of samples.

In some embodiments, a method for executing one or more computational workflows, the method comprises receiving, by a workflow execution service executing on a processor, a directed acyclic graph (DAG) representing a computational workflow. The DAG comprises a plurality of nodes and edges, wherein applications of the workflow comprise nodes and edges indicate the flow of data elements between applications. At least one application comprises an Application Programming Interface (API) script, the API script comprising a plurality of commands for controlling the workflow execution service via an API connected to the workflow execution service. Input is received from an end user via a Graphical User Interface (GUI) connected to the workflow execution service, and the computational workflow is executed in response to the received input.

BRIEF DESCRIPTION OF THE DRAWINGS

Various aspects and embodiments will be described with reference to the following figures. The figures are not necessarily drawn to scale.

DETAILED DESCRIPTION

Computational workflows can be built and executed using various interfaces to workflow processing systems, including but not limited to GUIs, APIs, and CLIs. However, the inventors have recognized that conventional techniques for building and executing computational workflows may be improved upon because each mode of interaction is separate from the other, leading to unique problems encountered by each. For example, conventional GUIs do not address common use cases, such as the ability to execute an automated series of workflows. Although, some workflow management systems can flatten such series of workflows into single tasks, such approaches are undesirable because they are exceedingly complicated and lack flexibility. Similarly, while an API or CLI may be used to execute such an automation, creating the set of commands to do so may be prohibitive for some users, and further may be difficult to execute in a simple manner.

Figure 1:
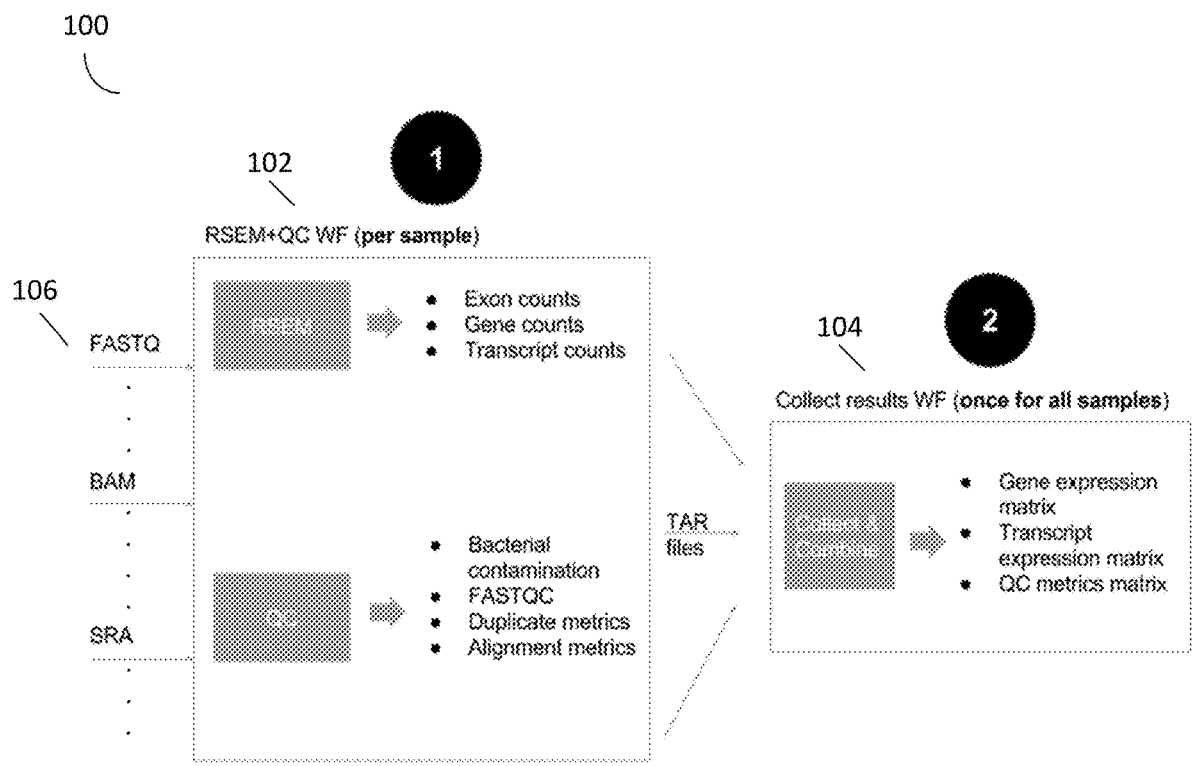
FIG. 1 illustrates the processing of a plurality of samples according to a first workflow and a second workflow.

For example, an end user may wish to process a plurality of samples according to a first workflow on a per-sample basis, resulting in a plurality of tasks in which the results for each sample are associated with each task. Subsequently, the end user may wish to collect the results from the first workflow and further process them using a single second workflow that is performed once for all of the samples. Each of these actions is typically performed by one or more functions of a workflow execution service. As shown in FIG. 1, one embodiment of an automation 100 of workflow execution service functions comprises executing a first workflow 102 individually for each of many individual samples 106, such as an RNA-Seq analysis workflow for a plurality of RNA-Seq samples (step 1). The results for each sample processed by the first workflow 102 are then collected and processed by a second workflow 104. However, conventional workflow execution service GUIs typically account only for the execution of single workflows, and may be unable to control and automate the execution of multiple workflows that depend on one another in this way. To accomplish this goal using a GUI, an end user could explicitly generate the automation 100 as a single monolithic workflow, which is difficult to build and maintain, is less modular (and thus less reusable), and tends to break more easily due to the increased number of constituent parts. Further, if one component of the workflow fails, the GUI may not include features allowing full or partial recovery; in some cases, all of the resulting data may be lost.

An end user can instead use an API to solve these problems programmatically. The API can be used to control and automate the execution of each of the first workflows 102 (e.g., using a loop), and then execute the second workflow 104 only when the first workflows 102 have completed and their outputs are available. Typically this comprises writing a sequence of API commands into a script, which may be executed by the end user to begin execution of the automation 100. Further, the API can be used to include additional error handling logic not implemented by the GUI, which can provide for the full or partial recoveries from component errors, resulting in an automation that is less fragile. For example, the end user may use the API to monitor or restart failed tasks, or adjust parameters, as needed to continue execution of the workflow during runtime.

However, the inventors have appreciated that scripting with an API is a localized activity that comes with its own problems. For example, API scripts are typically executed by external, heterogeneous client computers which interact with the workflow execution system over a network. As previously noted, the client computer typically lacks the persistence and stability of the workflow execution system, which is often subject to quality testing and validation, including extensive regression and integration testing. Client computers often have no logs, making it difficult to troubleshoot failures. Client machines are also subject to user error or misuse, and may inadvertently reboot, losing any records of the execution and making it difficult to re-start an analysis. Additionally, API scripts are often not directly portable between client machines due to missing or mismatching library dependencies. As such, an API script developed on one machine often fails to execute on another, and may require troubleshooting to get it running (which is difficult due to the aforementioned reason). Finally, as the API may include features not present in the GUI, those who lack the programming ability to use an API are unable to take advantage of these advanced features.

Accordingly, the inventors have developed a new class of techniques for building and executing computational workflows which provide for programmatic access and automation, while retaining the benefits of server-side execution, control, and ease of use. The new class of techniques can involve "wrapping" a sequence of API commands (i.e., an API script) as an application for execution on a workflow execution service. Executing the application via a second mode of interaction (such as the GUI or a CLI) provides several advantages over the single mode that improves the operation of both the second mode of interaction and the API script itself, including but not limited to: 1) the execution exists within a controlled execution environment (e.g., a virtualized image or container executing on a provisioned cloud instance); 2) enhanced reproducibility; 3) ease in co-development of workflows, as the API script may be stored within a wrapper (e.g., a CWL or WDL file) on the service; 4) ease of troubleshooting (all logs and error messages are stored on the service); 5) execution is independent of the user's computer, allowing a user to shut down their computer if needed and negating any potential for failure in the case of a connection problem; and 6) project-level management of analyses, as members in a project can run, monitor, and terminate analyses, as opposed to the single user executing the script.

Some embodiments described herein address all of the above-described issues that the inventors have recognized with conventional techniques for controlling workflow execution. However, not every embodiment described herein addresses every one of these issues, and some embodiments may not address any of them. As such, it should be appreciated that embodiments of the technology described herein are not limited to addressing all or any of the above-discussed issues of conventional techniques for controlling workflow execution. It should be appreciated that the various aspects and embodiments described herein may be used individually, all together, or in any combination of two or more, as the technology described herein is not limited in this respect.

I. Exemplary Workflow Execution Service

The general approach taken by embodiments of the present invention is illustrated in FIG. 2, which illustrates, in block-diagram form, an exemplary workflow execution service 200 with features enabling multiple modes of interaction to allow flexible, scalable, and accessible computational workflow executions. The service 200 may include a projects module 202, which allows end users (such as the end user 230) to create projects, or workspaces, on the service 200. Each project may serve as a container for information related to an analysis, including but not limited to data, files, workflows, users, and results. A file module 204 provides access to various data and files 205 on the service 200, and may further allow the end user 230 to upload, download, interact, and otherwise access data on the service. Files 205 made accessible by the file module 204 may be stored locally, such as on a local filesystem or database, or alternately may be stored on the "cloud," such as on a networked filesystem or available via a network connection, such as an Amazon Web Services (AWS) S3 bucket.

Various applications 207 may be made available for execution by the service 200 via the applications module 206. Applications 207 may include various POSIX compatible command line utilities for bioinformatics and genomics analyses, such as the Burrows-Wheeler Aligner (bio-bwa.sourceforge.net), Genome Analysis Toolkit (software.broadinstitute.org/gatk/), FastQC (www.bioinformatics.babraham.ac.uk/projects/fastqc/), and the like. Applications 207 may also include software for windows-based or other environments. Applications 207 are often stored using Docker™ containers, which provide a virtualized operating system that includes any dependencies or additional code required by that application. The applications module 206 may manage and configure the applications 207 to make them available for execution by the service 200. For example, the applications module 207 may define various features of an application, such as its location, required inputs, parameters, and the like.

Figure 3A:
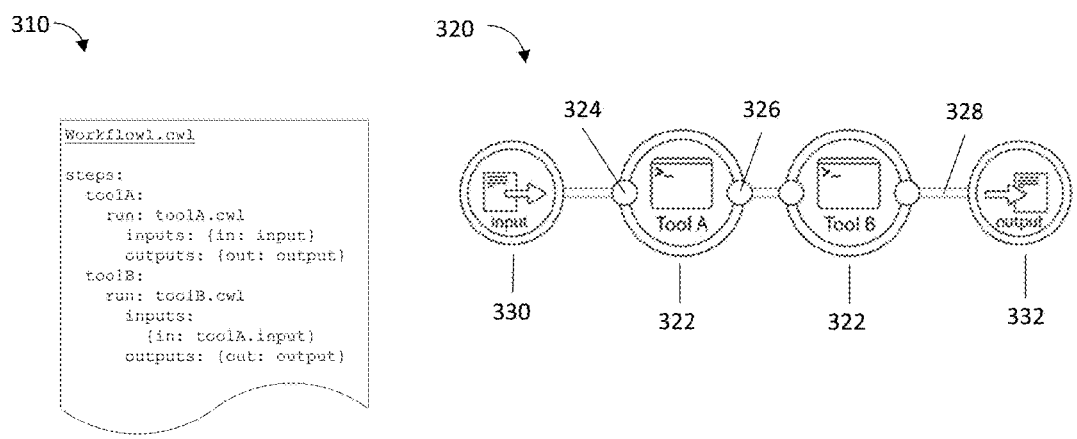
FIG. 3A depicts a computational workflow as a description and as a directed acyclic graph (DAG)

In additional to individual tools, applications 207 can also include computational workflows, which may comprise a series of applications or tools (including those already available on the service 200) interconnected such that an output of one tool is provided as an input to another. Workflows are typically represented as a directed acyclic graph (DAG), in which applications or components of the workflow become nodes and edges indicate the flow of data elements between linked tools. FIG. 3A illustrates an example of a workflow represented as a description 310 and as a DAG 320. As shown in FIG. 3A, the workflow description 310 includes two steps that describe executing the output from a first tool A using a second tool B. The workflow description 210 may be provided by the end user 230, or obtained from another source. The workflow description 210 can describe a computational workflow, such as a bioinformatics workflow, a genomics workflow, an engineering workflow, or any workflow requiring the execution of one or more applications. Computational workflows can comprise dozens of tools with hundreds of parameters to handle a variety of use cases and data types. In practice, workflows are described with machine-readable serialized data objects in either a general-purpose programming language, domain-specific language, or serialized object models for workflow description. For example, an object model-based approach may describe the steps in a workflow in JavaScript Object Notation (JSON) format with a custom syntax.

Similarly, the workflow description can be written using Common Workflow Language (CWL). CWL is a specification that allows one to describe various command line tools and to connect them together to create workflows. CWL is similar to tools such as GNU "make" as it specifies an order of execution based on dependencies between tasks. However, CWL further requires that tasks be isolated and have explicit values for both inputs and outputs. More information regarding CWL can be found at www.commonwl.org. Additionally, it should be noted that embodiments of the disclosure are not limited to CWL and may use a variety of formats of workflow descriptions, including Workflow Description Language (WDL), eXtensible Markup Language (XML), and the like.

Workflow descriptions typically describe a series of interconnected "steps", each of which can be a single tool (e.g., a command-line application executing in a POSIX environment) or another, previously-described, workflow. Each step in the workflow has a set of "ports" which represent data elements that are either inputs or outputs of the associated tool or workflow. A single port represents a specific data element that is required for execution of the tool, or is a product of the execution of the tool. For data elements which are passed between applications, there must be an output port from the upstream tool and a complementary input port on the downstream application. For example, a representation of the workflow description 310 as a DAG 320 includes two nodes 322 representing those tools. The nodes 322 have input ports 324 and output ports 326, which define discrete data elements, such as an input file 330, that are passed downstream along a set of edges 328 to generate a processed output 332.

Figure 3B:
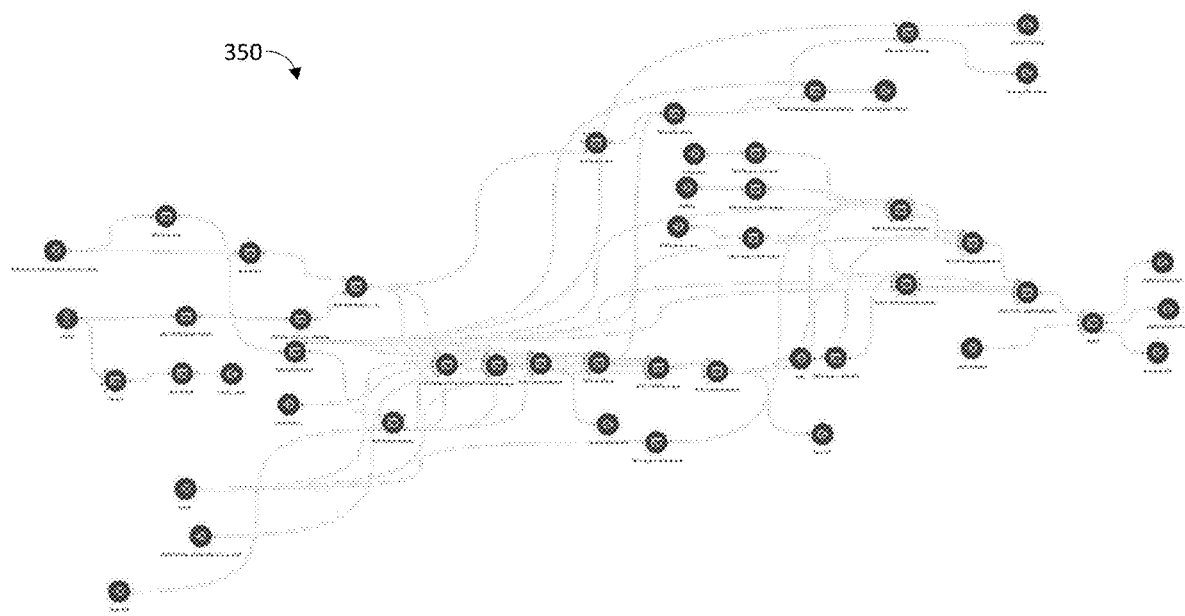
FIG. 3B depicts a DAG representing a workflow with a plurality of tools.

Such workflows can describe entire genomics analyses. FIG. 3B depicts an example of a DAG 350 describing a whole genome analysis to study the complete DNA sequence of an organism. One specific example of such a workflow is the Seven Bridges® "Multi-instance Whole Genome Sequencing GATK4.0 workflow", available in CWL format at igor.sbgenomics.com/public/apps. As shown, the DAG 350 contains dozens of interconnected tools providing various functionality related to quality control, file transformations, alignment, variant calling, and the like. Each of these tools may include specific optimizations, including the computational resource requirements of a tool, or an explicit recitation of the type of computational instance best suited for running that tool. In some cases, the workflow itself may include specific optimizations in order to obtain optimal usage of instance resources and avoid creating unnecessary processes. For example, the workflow may segment an alignment into several regions of the genome, which may individually be executed on a separate instance.

In practice, a workflow may be represented and stored in a computer memory. For example, a node can be a portion of a memory, which can include entries within a database, files or portions of one or more files within a file system, and the like. More specifically, a node can be one or more memory locations at which properties or characteristics of that node (e.g., fields associated with the associated step in the workflow description 210, such as the tool to be run and associated parameters) and references or relationships between that node and other nodes (e.g., the flow of data elements between steps) are stored. These relationships and references between nodes can be referred to as the edges of the graph. As a specific example, a node can be a portion of a memory at which a list of edges of that node (or edges adjacent to or incident upon that node) are stored.

Returning to FIG. 2A, the end user 230 can execute applications and workflows on the service 200 by submitting a request to the task executor 208. The request may include one or more applications, workflows, files, and parameters. The task executor 208 may then collect information from the request and create a task for execution. For purposes of the disclosure, a task refers to a defined unit of work performed by the service 200. A task typically comprises a combination of one or more files, applications, and parameters. Some tasks may comprise multiple workflows, such as if multiple workflows are embedded within a workflow (such as a nested workflow). Tasks may be submitted for execution on the service 200, on local computing resources, on a provisioned cloud instance, or on any suitable hardware. Once executed and completed, the outputs from a task may then be collected and presented to the end user 230, e.g. as one or more files organized into a project or workspace. In turn, the user may download, manipulate, or further analyze the results, e.g., via the analysis module 210, which may provide additional bioinformatics or computational analyses. This can include integration with an interactive programming notebook (e.g., a Jupyter Notebook), viewing of the results using a genome browser, or benchmarking variant calls, for example.

Figure 2A:
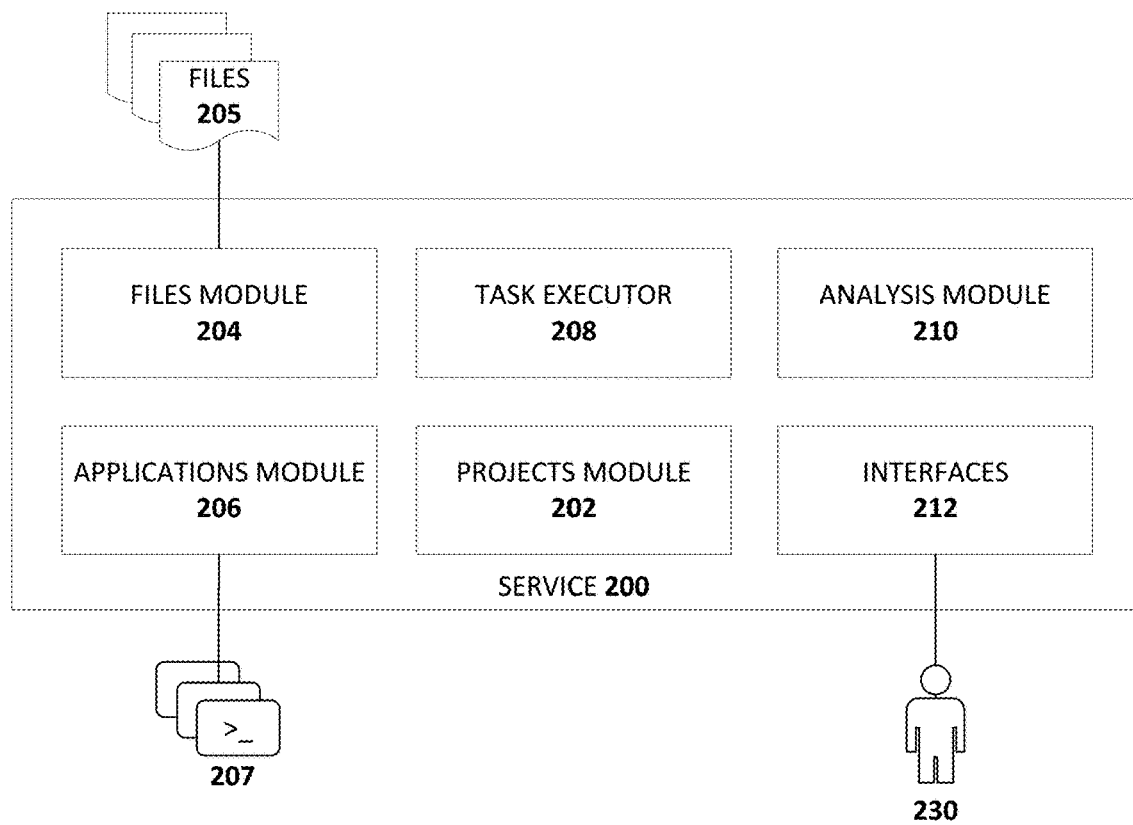
FIGS. 2A-B are block diagrams illustrating an embodiment of a representative workflow execution service according to the disclosure.
Figure 2B:
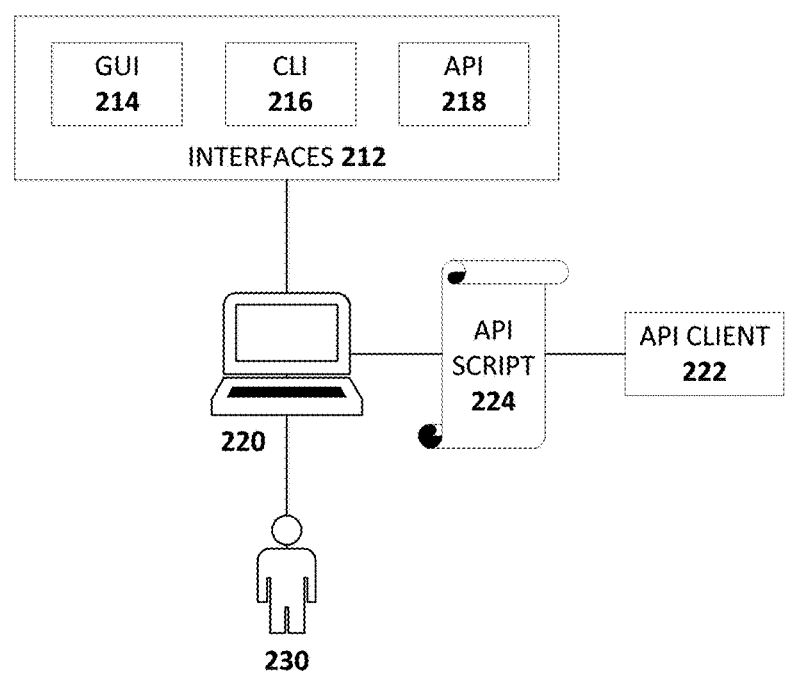

FIG. 2B illustrates different modes of interaction for the end user 230 to engage with the service 200. Typically, the end user 230 interacts with the service 200 using a client device 220, which may be connected to the service over a network. The end user 230 may interact with the service 200 using a variety of interfaces, including a Graphical User Interface (GUI) 212. In one embodiment, the GUI 212 can comprise an interactive web application made available over HTTP, and thus the end user 230 may interact with the service 200 visually using a web browser such as Microsoft Edge or Google Chrome. Using the GUI 212, the end user 230 can access links to create, access, delete, and otherwise manipulate projects, files, applications, and tasks in a point-and-click fashion. Computational workflows can be created (e.g., via the application module 206), submitted for execution as single tasks (via the task module 208), and analyzed for relevant outcomes (e.g., via the analysis module 212).

Alternately, the end user 230 may interact with the service 200 using a command line interface (CLI) 216. Like the GUI 214, the CLI 216 provides the end user with the ability to manipulate various portions of the service 200. However, per its name the CLI is used by manually typing a series of commands into a terminal or console, typically on a client device. For example, entering the command "projects create—name mRNA—description 'mRNA Sequencing Analysis Project'" would create a workspace in the service 200 with that description and name. Similarly, the commands "files list" or "apps list" would present the end user 230 with a list of files and apps available to that user, respectively. One advantage of the CLI 216 is that a series of commands can be pre-written and entered in sequence, allowing for some automation of service 200 functions. Like the GUI 214, the CLI 216 is typically accessed by the end user 230 via a client device 220, such as the end user's own workstation or laptop, which may include certain libraries or applications developed for accessing the CLI 216 on the service 200. End users who prefer programmatic access to service 200 functions may prefer the CLI 216 over the GUI 214.

Another interface 212 to the service 200 is the Application Programming Interface (API) 218. Like the CLI 216, the API 218 provides a programmatic way to access, configure, and interact with the service 200. The API 218 may be implemented using the Representational State Transfer (REST) architectural style, in which resources and functions on the service 200 are requested over HTTP and information is returned in, e.g., JavaScript Object Notation (JSON) format. For example, a RESTful URL directed to the service 200 and including the suffix "/tasks/list" would return information to the end user 230 describing those tasks available to the end user, and a URL including the suffix "/tasks/123" would return information about a specific task having the identifier "123". Like the CLI 216, the API 218 may be preferred by end users who desire programmatic access to the service 200, and typically requires the use of a client machine to access. Additionally, the API 218 may be used to integrate the workflow execution service 200 with other environments, such as a Laboratory Information Management System (LIMS), and to automate various procedures, such as uploading files, querying metadata, executing tasks, and performing analyses. One common client software for accessing and interacting with such an API is "Postman", available at www.getpostman.com.

It should be noted that FIGS. 2A-B depict only a single embodiment of a workflow execution service. In other embodiments, the configuration of the modules may vary; for example, a service may have one or less modules, or include additional modules comprising a variety of features. Various embodiments are considered to be within the scope of the disclosure.

II. API Clients

The API 218 may be further extended by the use of an API client 222, which allows end users to automate, extend, and further customize their analysis workflows and interactions with the service 200 by writing an API script 224. An API client may be essentially a "wrapper" for the API 218 that is written in a particular programming language. For example, one may write a set of bindings in the Python, R, or Java programming languages that correspond to each of the various API 218 calls, allowing for the incorporation of API 218 calls into a script or program written in that language.

The use of an API client 224 is a powerful feature. An API client 224 allows the end user 230 to chain API commands together, providing for scripting and automation of various features on the service 200. For example, an API script 222 can include steps directed towards file uploads, project management, metadata capture, quality control checks, execution of tools and workflows, and handling of the resulting data—in ways that are not possible using either the GUI or CLI. Further, an API client 224 allows for the integration of the service 200 with varied other services. For example, the API client 224 can be used to access files 205 from a networked or cloud data source, such as an AWS bucket. Similarly, the API client 224 can be used to integrate the service 200 with other systems or services, such as a Laboratory Information Management System (LIMS). In this way, the API client 224 offers many advantages over the GUI via programmatic access and automation, allowing for the creation of complex processes and workflows that would not be practicable or cost efficient to implement as a GUI feature.

The API is typically used in situations where a feature is not enabled in the GUI or CLI, or where more advanced programmatic control is desired. For example, in the automation 100 of FIG. 1, each sample 106 processed by the first workflow 102 comprises a single task. The results of each task may then be collected by the second workflow 104 for further processing. This automation 100 can be performed by certain GUIs which allow for batch processing, or scatter/gather techniques, and thus compress or "flatten" the automation 100 into a single task. However, this typically results in a fragile workflow. If one component of the workflow fails, the GUI may not include features allowing full or partial recovery. In some cases, all of the resulting data may be lost, or may need to be re-computed, reducing scalability. By using an API client 222, the end user 230 can include additional error handling logic not available via a GUI, which can provide for full or partial recoveries from component errors, resulting in an automation that is more stable. For example, the end user may use the API to monitor or restart failed tasks, or adjust parameters, as needed, to traverse error conditions and continue successful execution of the workflow during runtime.

API clients 222 further allow for the incorporation of user-generated logic. For example, an end user may wish to run a workflow in which tasks are conditionally performed, such as based on the input file type. If a file input type is "FASTQ", then a workflow that expects the FASTQ format as input should be executed. However, if the input type is "BAM" or "SRA", then alternate workflows should be executed to accommodate those different formats. However, conditional logic is often not implemented in GUIs as it is fairly complex and hard to account for all use cases. Typically, an end user would have to be careful that all selected files match the expected file type, before starting execution of a workflow.

In contrast, this conditional logic can be incorporated into an API script. As shown in Table 1 below, an API script can be written that includes logic statements related to different input types. Depending on the file input type, a modified version of the workflow may be run that accommodates that particular input type, or includes additional steps (e.g., file conversion).

TABLE 1

Conditional logic for different file input types. Depending on the file input type, a different version of the "RSEM + QC" workflow is selected for execution.

| Logic Statement | File Input Type | Run this workflow |
|---|---|---|
| IF | FASTQ | RSEM + QC from FASTQ |
| ELIF | BAM | RSEM + QC from BAM |
| ELSE | SRA | RSEM + QC from SRA |

API scripting allows for the incorporation of various custom logic into workflow execution systems. Additional logic that can be executed using an API script includes, but is not limited to, 1) conditionals (e.g., IF×THEN run workflow-1; ELSE run workflow-2); 2) loops and chaining (e.g., FOR sample IN samples run workflow-1 (sample); run workflow-2); 3) incremental re-runs (e.g., can inspect existing outputs before running a workflow); 4) automatic retries (e.g., after Docker or instance-related failures); and 5) automated file renaming and setting of tags, metadata, imports, and exports. Another similar situation arises when different versions of workflows may be executed based on input parameters. For example, an API script can specify that the RNA-Seq software to use is "STAR Version 2.5.1b" when the input parameter indicates so; otherwise, it can execute an alternate version (e.g., "STAR version 2.4"). Thus, API scripting provides for fine-grained detail and control of workflow scripting and automation, and can be used for nearly any use case.

Figure 4:
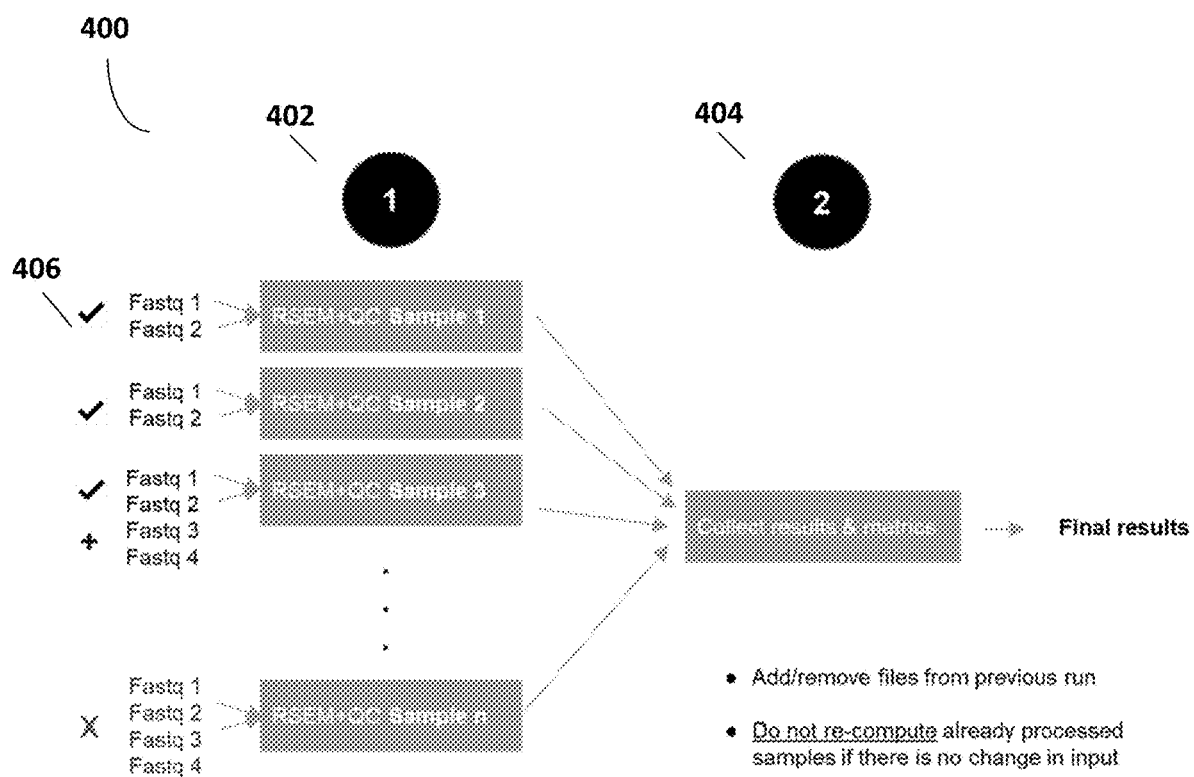
FIG. 4 illustrates the processing of a plurality of samples according to a first workflow and a second workflow.

API scripting can also provide sophisticated management of service 200 features, particularly with respect to organizing and managing task execution. FIG. 4 depicts a multi-step automation 400 that, like the automation 100 of FIG. 1, processes a plurality of samples according to a first workflow 402, and subsequently collects the results for each and provides a final output by processing through a second workflow 404. In such a multi-step workflow, an end user may wish to make changes to, remove, or add a subset of samples 406 after the automation 400 has already completed. For example, an end user may determine based on the final result that a subset of the samples were unsatisfactory, or may need to be re-processed due to too few reads or failure to pass a QC check. Further, the end user may wish to make changes without necessarily re-processing all unchanged samples, and then paying additional costs for compute.

Using a GUI, if the end user wanted to avoid re-running all samples and instead wished to process only those samples that changed or failed during the first round of workflow execution, she would likely need to manually select those that were unsatisfactory out of the potentially hundreds or thousands of samples. Manually adding/removing samples from a workflow using a GUI is a tedious process, particularly as samples consist of several files each, which are not typically intuitively categorized on a per-sample basis. Importantly, re-processing of only a subset of samples would result in incomplete results in Step 2 of the automation 400, which should always collect results from all samples, both from the ones previously executed and from the samples that need (re-)processing. An API script can capture this incremental execution logic by, e.g., including steps directed to checking whether files exist in a certain project, whether a certain file has already been processed, whether a file has changed since a previous execution, etc.

III. Integration of API Scripting with other Service Features

As previously noted, API scripts by their nature may be executed on a client device 220 separate from the service 200, e.g. as illustrated in FIG. 2B. Such client devices typically lack the reliability of the service 200, which in a production environment is subject to extensive testing, multiple levels of redundancy, and the like. Client devices are typically heterogenous and may be hard to troubleshoot; further, they are subject to user error or misuse, and may inadvertently reboot, crash, or hang, and thus are prone to loss of information for any analyses performed. Accordingly, the inventors have recognized and appreciated that these problems may be solved by incorporating an API script directly into a workflow execution service, which provides several advantages over traditional methods over singular interface workflow execution that improves the operation of both the API and other modes of interaction together.

Figure 5A:
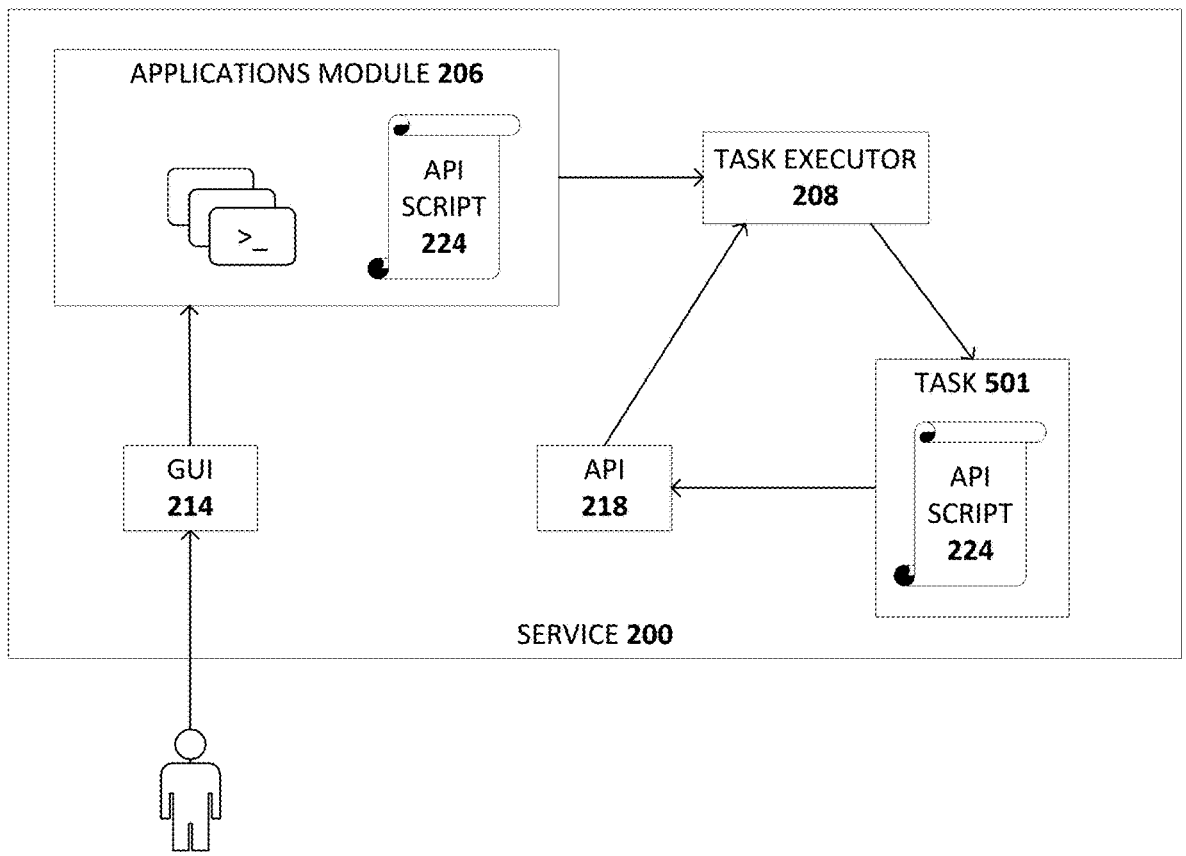
FIGS. 5A-B are block diagrams illustrating interactions of an end user and an API script with a workflow execution service according to the disclosure.

FIG. 5A illustrates a method of interacting with a workflow execution service according to an embodiment of the disclosure. As shown in FIG. 5A, instead of executing an API script 224 on a client device 220, the API script can instead by configured for execution on the workflow execution service itself, similar to the other applications 207. Configuring the API script 224 for execution can comprise "wrapping" the API script using a workflow definition language, such as Common Workflow Language (CWL, www.commonwl.org). Once the API script 224 is wrapped, the end user 230 may use the GUI 214 (or CLI 216 of FIG. 2) to create a task 501 including the API script 224 and submit it for execution to the task executor 208.

Figure 5B:
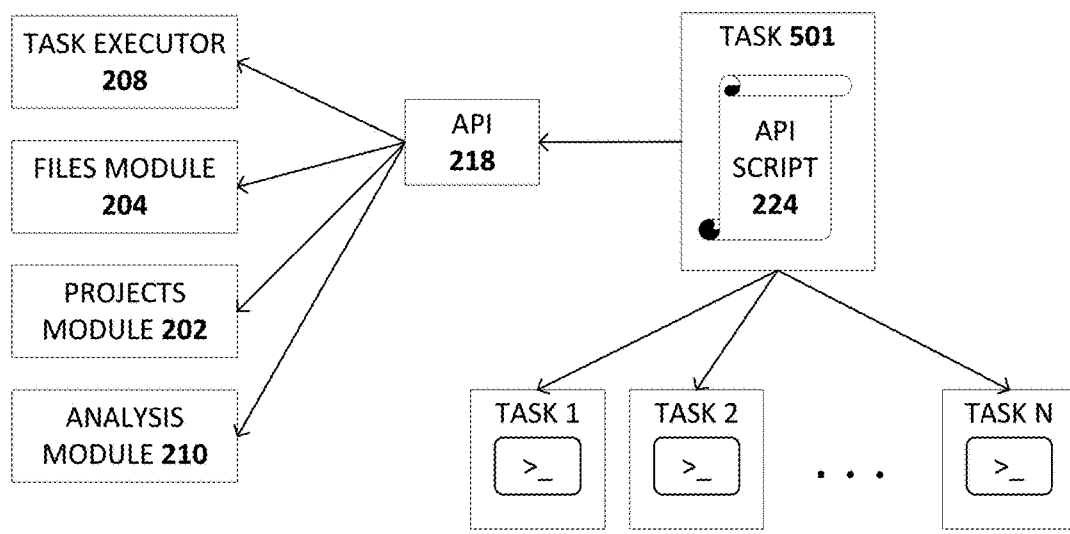

Once executed, the task 501 including the API Script 224 can interact directly with the API 218 in order to perform complex analyses, entirely executing on the service 200 without requiring the use of a secondary client device 220. For example, the API script 224 may use the API 218 to further interact with the task executor 208. As shown in FIG. 5B, such a task 501 can use the API 218 to interact with all or nearly all functions available on the service 200, including the analysis module 210, projects module 202, files module 204, and task executor 208, for example. The API script may use these functions to create, manage, monitor, and re-try additional tasks (1, 2, . . . N), pull input files from internal or external infrastructure, configured required metadata for input files, and deliver compute results both to the service 200, as well as external services.

In this way, the workflow execution service 200 is instructed by an end user 230 via the GUI to initiate execution of an application. In turn, the application, when executed as a task 501, further instructs the workflow execution service 200 to perform more advanced tasks and logic. By virtue of the executed API script, the workflow execution service 200 is essentially instructing itself to perform additional tasks and configure different modules and services. This results in a unique integration of multiple modes of interaction, allowing for complex analyses to be initiated using a simple visual interface.

One additional benefit of incorporating an API script 224 into task execution within the service 200 is the ability to integrate elements unique to other modes of interaction, such as using the GUI 214 to visually select and specify input files and parameters for tasks instead of providing a long list of command-linen parameters. For example, consider an API script that requires a list of previously uploaded data files as input. An end user would simply upload the list as a single file (e.g., as a spreadsheet or other structured document), select this as input for the tool, and begin execution. This feature is particularly helpful when dealing with GUI limitations, such as the long time required to select many input files for analysis. Instead, relevant information an be captured into a structured document, and then supplied by the end user via the GUI as a single input to the wrapped API script.

Figure 6:
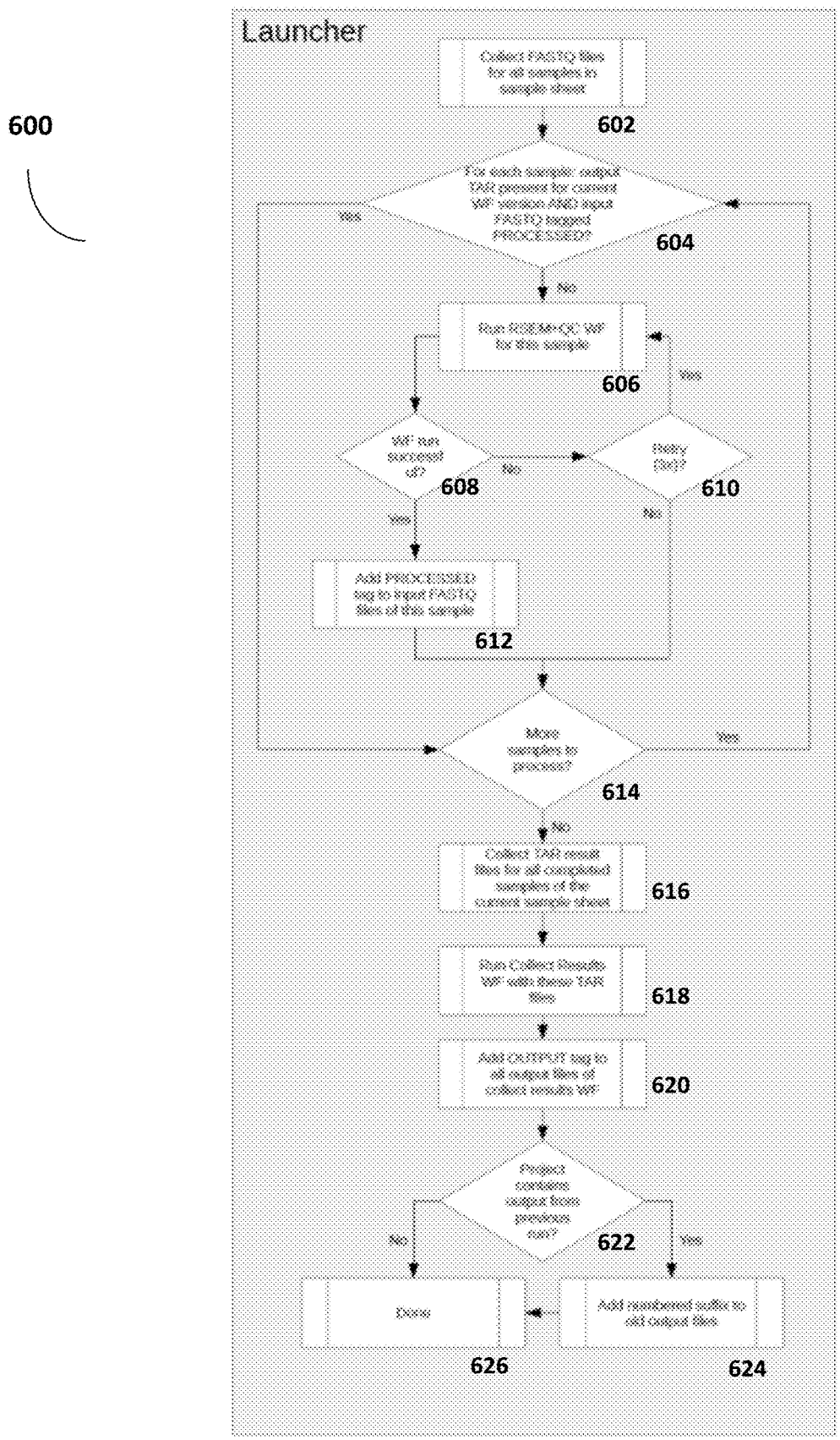
FIG. 6 is a flow diagram depicting an embodiment of a method for processing one or more computational workflows by an API script.

FIG. 6 illustrates actions taken by an API script, in concert with GUI elements, for processing a computational workflow by a workflow execution service. The API Script defines an automation 600 for performing various functions of a workflow execution service according to the disclosure. First, a set of FASTQ files for a plurality of samples are collected via a single sample sheet provided by the end user via the GUI (step 602). The script then determines whether an output file is already available and whether the input files are already marked as processed (decision 604). Each sample is then processed (if it hasn't been already) by executing a certain workflow for that sample (step 606), such as an RSEM+QC workflow. If the workflow was not successful (decision 608), it may be re-tried multiple times (decision 910). Once successful, a "processed" tag or metadata field may be added to the input file for that sample, informing future executions as to whether that sample has already been processed (step 612). Once all samples have been processed (decision 614), the output files from each of the workflows for each sample are collected (step 616), provided to a second workflow for execution (step 618), and certain metadata fields are updated to the output files to indicate that they have been processed by the second workflow (step 620). Finally, if there are conflicts between generated files (decision 622), the naming of the output files are distinguished, e.g., by a numbered suffix (step 624). Finally, the automation 600 is complete (step 626). Importantly, many of these steps are custom to the performed analysis, so solving this with a generic or GUI-based solution can be challenging, if not impossible.

Figure 7:
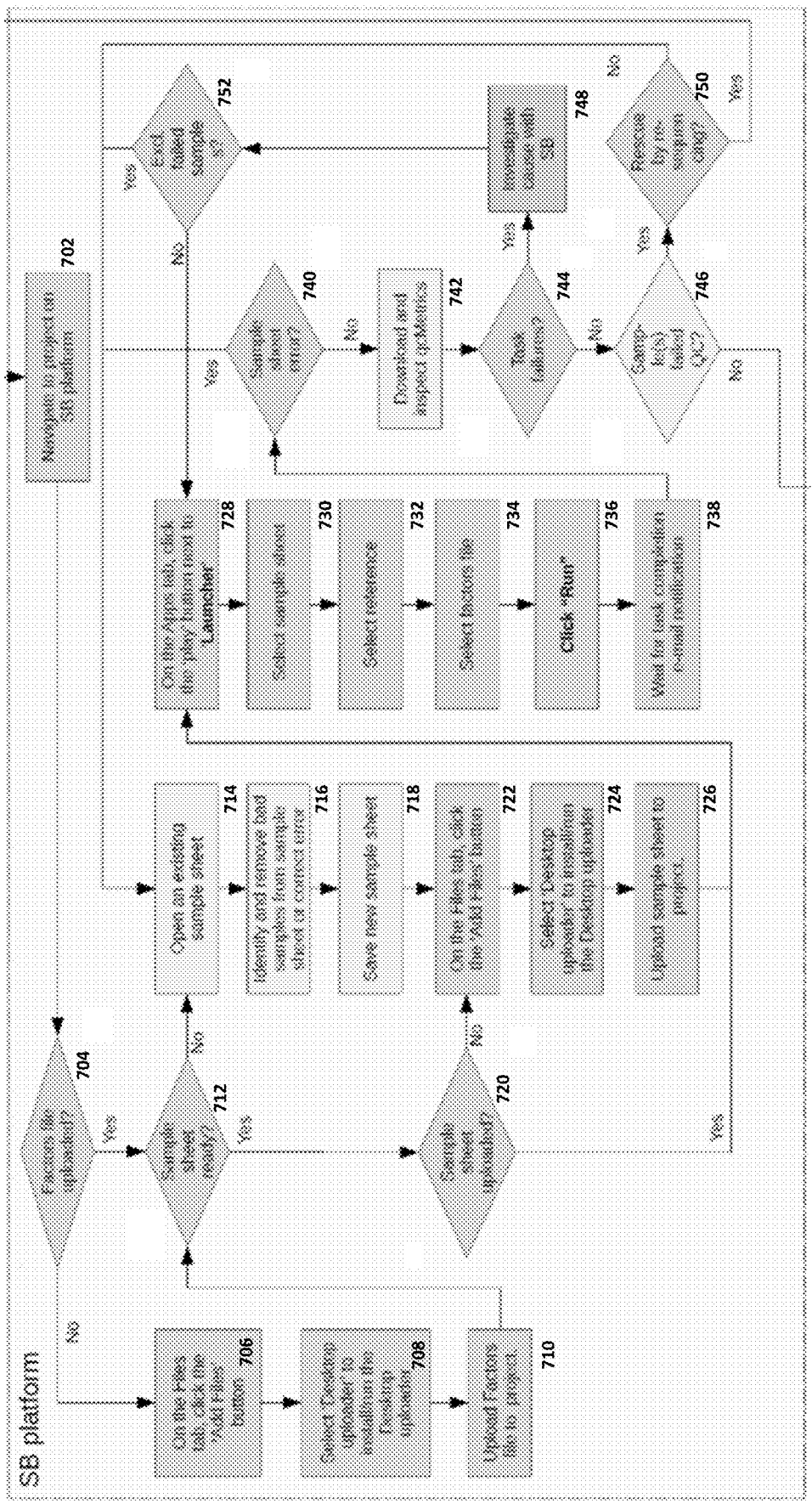
FIG. 7 is a flow diagram depicting an end user flow for interacting with a GUI to execute an API script on a workflow execution service according to the disclosure

FIG. 7 illustrates the corresponding actions taken by an end user interacting with a GUI to execute the API script of FIG. 6. Using the GUI, the end user navigates to a project on the service (step 702), and if needed uploads a metadata file (decision 704; steps 706, 708, 710). Next, the end user either creates a new sample sheet by modifying and saving a previous copy (decision 712; steps 714, 716, 718), or uploads a copy by adding a file and uploading to the service (decision 720; steps 722, 724, 726). Once the sample sheet and metadata files are confirmed, the end user navigates using the GUI to select the API script for execution, which is wrapped as an application on the service 200 (step 728). The sample sheet, metadata files, and reference genome (e.g., the human reference genome) are provided as inputs to the wrapped API script (steps 730, 732, 734), and the user then submits the automation for execution by clicking "Run") (step 736). Once complete, the user may receive an e-mail notification (step 738) (e.g., which may be specified by the corresponding API script), address any errors with the sample sheet (step 740), perform QC (step 742), determine whether any tasks (step 744) or samples (step 746) failed or failed QC checks, and take any necessary downstream actions, such as further investigating the cause (step 748) and potentially excluding the failed samples (step 750), or rescuing the sample by performing re-sequencing (decision 752).

Figure 8A:
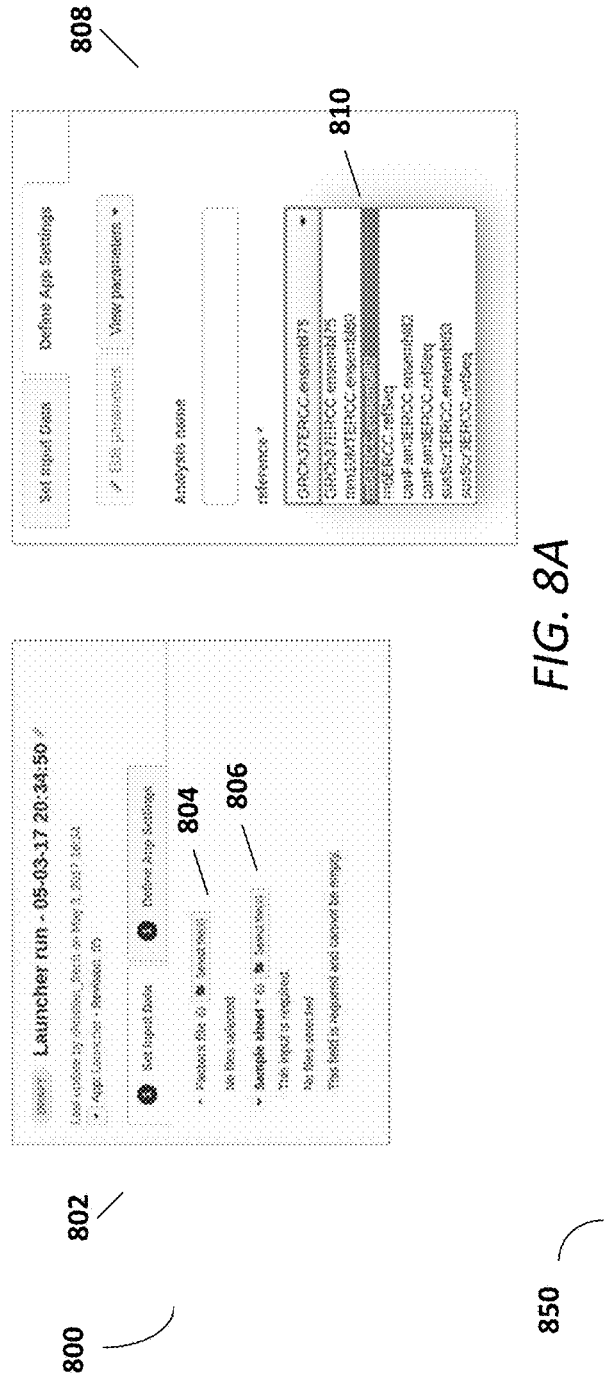
FIG. 8A illustrates a representative GUI for receiving input from an end user for providing to an API script.
Figure 8B:
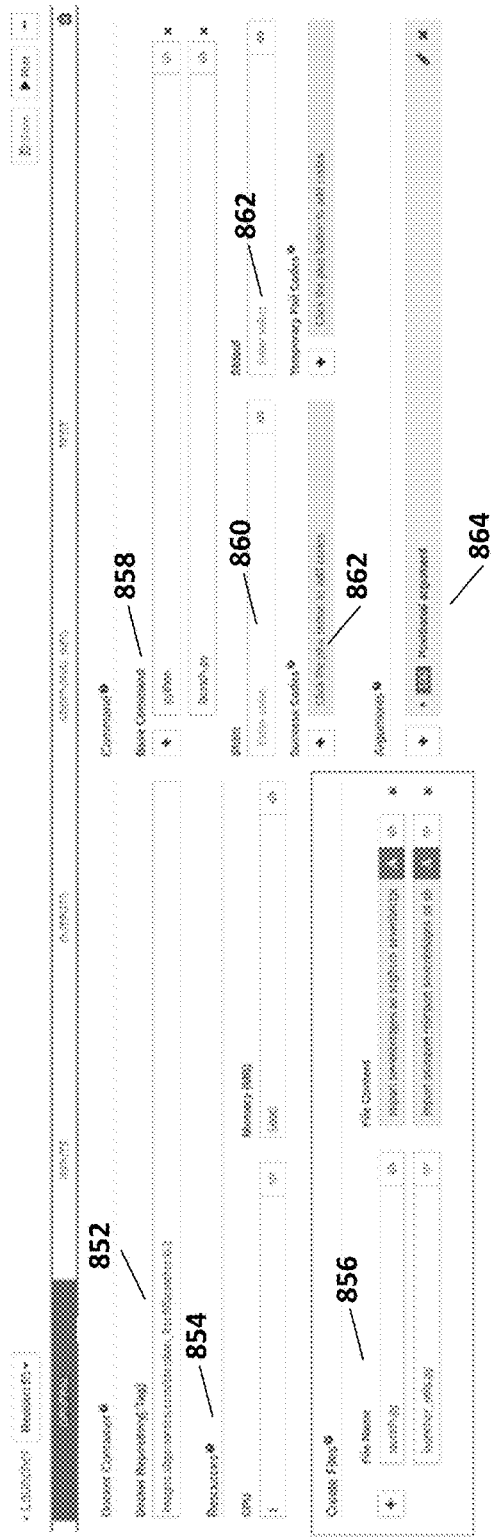
FIG. 8B illustrates a representative GUI for configuring an API script for execution on a workflow execution service.

FIG. 8A further illustrates the integration of the API script into a GUI 800. As shown in FIG. 8A, a first window 802 allows for the end user to select files for processing by the API script, such as options for a metadata file 804 and sample sheet 806. Subsequently, a second window 808 may provide the end user with an option to select a reference genome 810, such as the rat genome from ENSEMBL. These options are enabled by wrapping the API script for execution on the service. For example, as shown in FIG. 8B, an end user may use a GUI 850 to specify an API script for execution from a Docker container 852, set resource requirements 854, and include any needed helper scripts 856, a base command 858, required inputs 860 or outputs 862, success codes 864, and arguments 866. In this way, the API script is integrated into the GUI, combining elements from both interfaces and significantly increasing the capabilities of the workflow execution service. End users may run complex workflows and analyses available only through API scripting, but which may be embodied as a simple "1-click" solution available only through the GUI.

Figure 9:
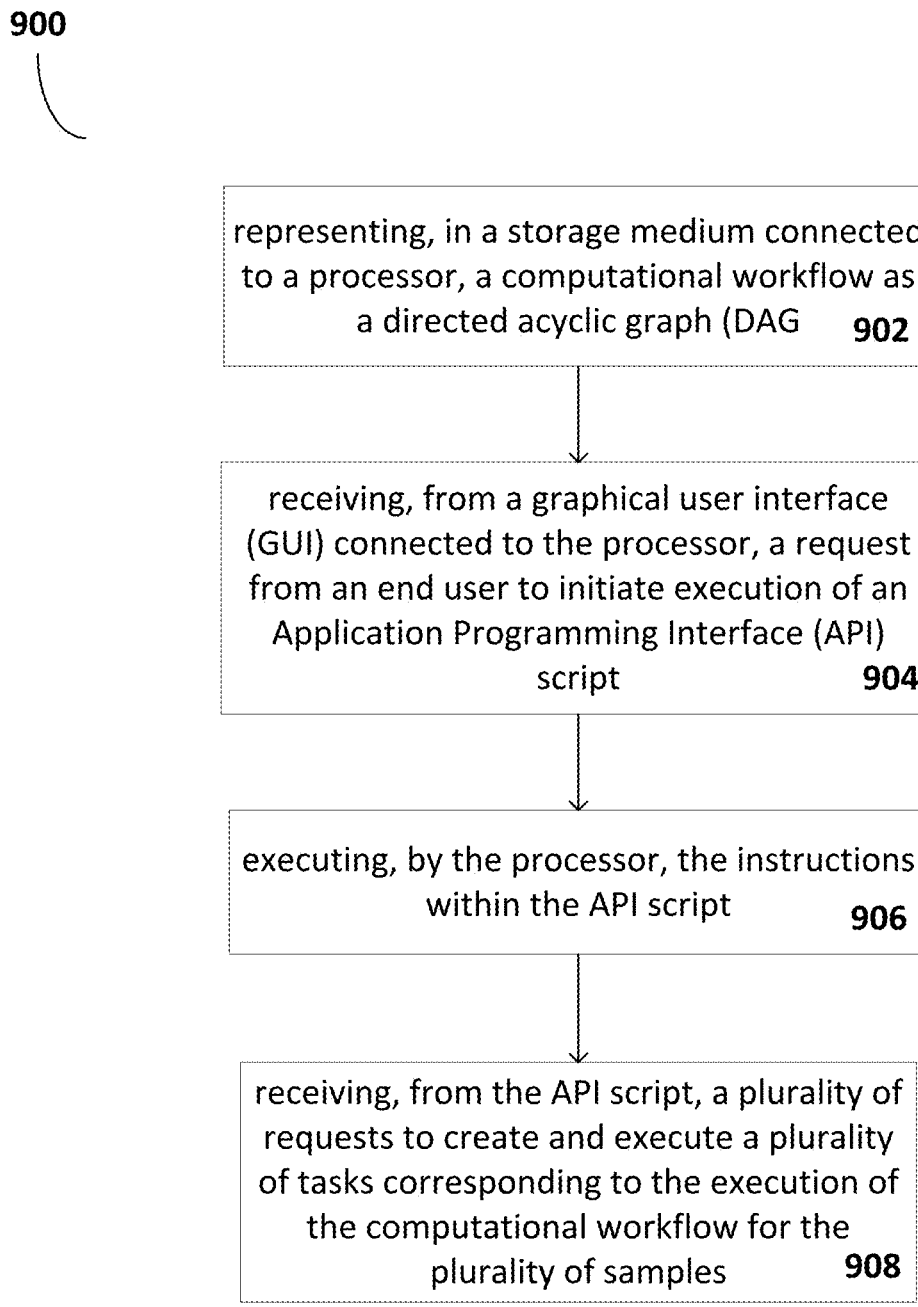
FIG. 9 is a flow diagram depicting an embodiment of a method for processing one or more computational workflows according to the disclosure.

FIG. 9 depicts an embodiment of a method 900 of processing one or more computational workflows according to the disclosure. The method 900 can begin by representing, in a storage medium connected to a processor, a computational workflow as a directed acyclic graph (DAG) (step 902). In the DAG, applications may be represented as nodes, and edges may connect the nodes to indicate the flow of data elements between linked applications. The method 900 continues by receiving, from a GUI connected to the processor, a request from an end user to initiate execution of an API script (step 904). The API script may comprise instructions to direct a task execution module connected to the processor to create and execute a plurality of tasks corresponding to the execution of the computational workflow for a plurality of samples. In response to the request, the processor executes the instructions within the API script (step 906). In turn, the processor receives a plurality of requests to create and execute a plurality of tasks corresponding to the execution of the computational workflow for the plurality of samples (step 908).

IV. Computer Systems

Figure 10:
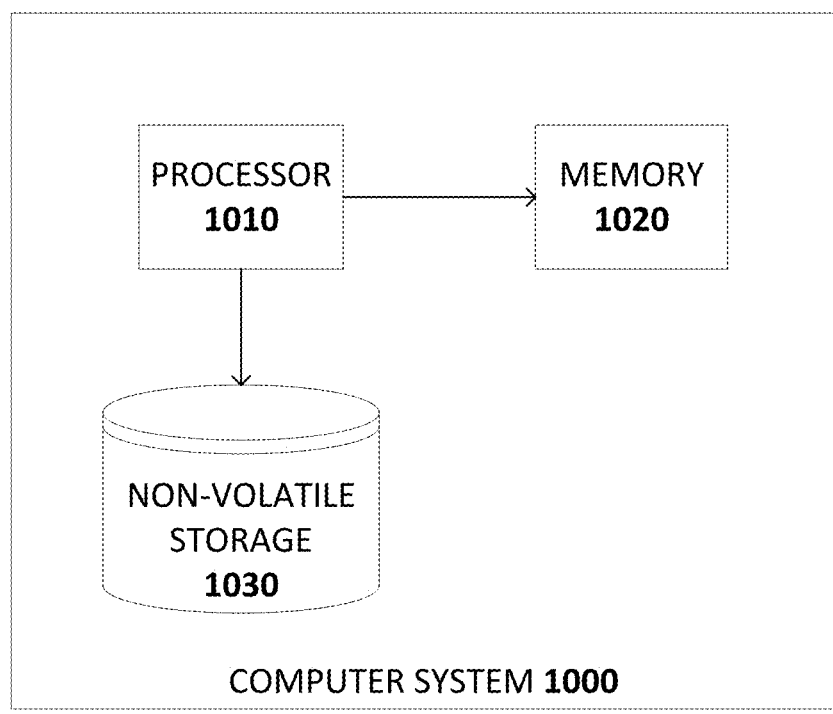
FIG. 10 is a block diagram of an illustrative computer system that may be used in implementing some embodiments of the technology described herein.

An illustrative implementation of a computer system 1000 that may be used in connection with any of the embodiments of the disclosure provided herein is shown in FIG. 10. The computer system 1000 may include one or more processors 1010 and one or more articles of manufacture that comprise non-transitory computer-readable storage media (e.g., memory 1020 and one or more non-volatile storage media 1030). The processor 1010 may control writing data to and reading data from the memory 1020 and the non-volatile storage device 1030 in any suitable manner, as the aspects of the disclosure provided herein are not limited in this respect. To perform any of the functionality described herein, the processor 1010 may execute one or more processor-executable instructions stored in one or more non-transitory computer-readable storage media (e.g., the memory 1020), which may serve as non-transitory computer-readable storage media storing processor-executable instructions for execution by the processor 1010.

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples have been provided including with reference to FIG. 5. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A system for processing one or more computational workflows, the system comprising:
   a non-transitory storage medium connected to a processor;
   a description of a computational workflow, stored in the storage medium, the computational workflow comprising a directed acyclic graph (DAG) in which applications are represented as nodes and edges connecting the nodes indicate the flow of data elements between linked applications;
   a task execution module configured to create and execute tasks, wherein a single execution of the computational workflow comprises a single task;
   an application programming interface (API) in communication with the task execution module, the API comprising a plurality of function calls for controlling at least one function of the task execution module;
   an API script, stored in the storage medium, for automating functions of the task execution module, the API script comprising instructions to the API to create and execute a plurality of tasks corresponding to the execution of the computational workflow for a plurality of samples;
   a graphical user interface (GUI) in communication with the task execution module, wherein the GUI is configured to receive input from an end user to initiate execution of the API script.

2. The system of claim 1, wherein the API script further comprises instructions to collect the outputs of the computational workflow for each of the plurality of samples, and process the outputs using a second computational workflow.

3. The system of claim 1, wherein the API script further comprises instructions to determine whether a sample of the plurality of samples has already been processed by the computational workflow.

4. The system of claim 1, wherein the API script requires one or more input files for execution, and the GUI is further configured to receive the one or more input files from the end user.

5. The system of claim 4, wherein the one or more input files from the end user comprises a sample sheet defining the location of the plurality of samples to be processed by the computational workflow.

6. The system of claim 1, wherein the API script further comprises instructions to execute a different computational workflow for a sample depending on characteristics of the sample.

7. The system of claim 6, wherein the characteristic of the sample considered by the API script is the file format for the sample.

8. The system of claim 1, wherein each sample comprises a data file, each data file comprising a plurality of DNA sequence reads.

9. The system of claim 1, wherein the API script further comprises an API client, wherein the API client comprises a plurality of wrappers for API calls.

10. The system of claim 1, wherein the instructions in the API script further comprise monitoring the plurality of tasks, identifying a task that has failed, and restarting the failed task.

11. The system of claim 1, wherein the instructions in the API script further comprise retrieving a data file for task corresponding to a sample from an external resource.

12. A method for executing one or more computational workflows, the method comprising:
   representing, in a storage medium connected to a processor, a computational workflow as a directed acyclic graph (DAG) in which applications are represented as nodes and edges connecting the nodes indicate the flow of data elements between linked applications;
   receiving, from a graphical user interface (GUI) connected to the processor, a request from an end user to initiate execution of an Application Programming Interface (API) script, wherein the API script comprises instructions to direct a task execution module connected to the processor to create and execute a plurality of tasks corresponding to the execution of the computational workflow for a plurality of samples;
   executing, by the processor, the instructions within the API script; and receiving, from the API script, a plurality of requests to create and execute a plurality of tasks corresponding to the execution of the computational workflow for the plurality of samples.

13. The method of claim 12, wherein the API script further comprises instructions to collect the outputs of the computational workflow for each of the plurality of samples, and process the outputs using a second computational workflow.

14. The method of claim 12, wherein the API script further comprises instructions to determine whether a sample of the plurality of samples has already been processed by the computational workflow.

15. The method of claim 12, wherein the API script requires one or more input files for execution, and the GUI is further configured to receive the one or more input files from the end user, wherein the one or more input files from the end user comprises a sample sheet defining the location of the plurality of samples to be processed by the computational workflow.

16. The method of claim 12, wherein the API script further comprises instructions to execute a different computational workflow for a sample depending on a characteristic of the sample, wherein the characteristic of the sample considered by the API script is the file format for the sample.

17. The method of claim 12, wherein each sample comprises a data file, each data file comprising a plurality of DNA sequence reads.

18. The method of claim 12, wherein the API script further comprises an API client, wherein the API client comprises a plurality of wrappers for API calls.

19. The method of claim 12, wherein the instructions in the API script further comprise monitoring the plurality of tasks, identifying a task that has failed, and restarting the failed task.

20. A method for executing one or more computational workflows, the method comprising:
receiving, by a workflow execution service executing on a processor, a directed acyclic graph (DAG) representing a computational workflow, the DAG comprising a plurality of nodes and edges, wherein applications of the workflow comprise nodes and edges indicate the flow of data elements between applications;
wherein at least one application comprises an Application Programming Interface (API) script, the API script comprising a plurality of commands for controlling the workflow execution service via an API connected to the workflow execution service;
receiving input from an end user via a Graphical User Interface (GUI) connected to the workflow execution service; and
executing the computational workflow in response to the received input.

* * * * *